United States Patent
Nam et al.

(10) Patent No.: US 11,084,771 B2
(45) Date of Patent: Aug. 10, 2021

(54) METHOD FOR PURIFYING PHENOL

(71) Applicant: LG CHEM, LTD., Seoul (KR)

(72) Inventors: Hyun Nam, Daejeon (KR); Young Ho Lee, Daejeon (KR); Ki Yong Yoon, Daejeon (KR); Jun Hyuk Lim, Daejeon (KR); Kyung Moo Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 204 days.

(21) Appl. No.: 15/778,584

(22) PCT Filed: Jan. 11, 2018

(86) PCT No.: PCT/KR2018/000545
§ 371 (c)(1),
(2) Date: May 23, 2018

(87) PCT Pub. No.: WO2018/139787
PCT Pub. Date: Aug. 2, 2018

(65) Prior Publication Data
US 2021/0198170 A1  Jul. 1, 2021

(30) Foreign Application Priority Data
Jan. 24, 2017  (KR) .................. 10-2017-0011269

(51) Int. Cl.
*C07C 37/86* (2006.01)
*C07C 37/78* (2006.01)

(52) U.S. Cl.
CPC .............. *C07C 37/86* (2013.01); *C07C 37/78* (2013.01)

(58) Field of Classification Search
CPC .................................. C07C 37/86; C07C 37/78
See application file for complete search history.

(56) References Cited

U.S. PATENT DOCUMENTS

| | | | |
|---|---|---|---|
| 3,029,294 A * | 4/1962 | Keeble | C07C 37/86 203/29 |
| 3,965,187 A | 6/1976 | Little et al. | |
| 6,486,365 B1 | 11/2002 | Fulmer et al. | |
| 7,034,192 B2 | 4/2006 | Wijesekera | |
| 2005/0215834 A1 | 9/2005 | Wijesekera | |
| 2005/0215835 A1 | 9/2005 | Wijesekera et al. | |
| 2005/0222466 A1 | 10/2005 | Tatake et al. | |
| 2012/0053173 A1 | 3/2012 | Banno et al. | |
| 2012/0270865 A2 | 10/2012 | Banno et al. | |
| 2015/0065755 A1 | 3/2015 | Shirahata et al. | |

FOREIGN PATENT DOCUMENTS

| | | |
|---|---|---|
| CN | 1656052 A | 8/2005 |
| CN | 1938250 A | 3/2007 |
| CN | 101421213 A | 4/2009 |
| CN | 101993427 A | 3/2011 |
| CN | 102015641 A | 4/2011 |
| EP | 1847523 A1 | 10/2007 |
| GB | 1381398 A | 1/1975 |
| KR | 1020080093463 A | 10/2008 |
| KR | 10-2011-0134075 A | 12/2011 |
| KR | 101378274 B | 4/2014 |
| KR | 101602594 B1 | 3/2016 |
| WO | 2007118600 A1 | 10/2007 |

OTHER PUBLICATIONS

Carlsson et al., "Synthesis and Preliminary Characterization of a Novel Antiarrhythmic Compound (KB130015) with an Improved Toxicity Profile Compared with Amiodarone", Journal of Medicinal Chemistry, Jan. 3, 2002, pp. 623-630, XP055109284.

Morizur et al., "Catalysis of the acylation of aromatic derivatives by metallic tosylates", Tetrahedron, vol. 71, No. 38, pp. 6813-6817 (2015).

* cited by examiner

*Primary Examiner* — Rosalynd A Keys
(74) *Attorney, Agent, or Firm* — Dentons US LLP

(57) ABSTRACT

The present invention relates to a method for purifying phenol, which comprises: contacting a phenol stream comprising hydroxyacetone, 2-methylbenzofuran, 3-methylbenzofuran and phenol with an acyl chloride in the presence of an organic sulfonic acid to convert one or more selected from the group consisting of hydroxyacetone, 2-methylbenzofuran and 3-methylbenzofuran into a high boiling point compound having a boiling point higher than that of the phenol; and recovering the high boiling point compound from the phenol stream.

8 Claims, No Drawings

METHOD FOR PURIFYING PHENOL

CROSS-REFERENCE TO RELATED APPLICATIONS

This application is a National Stage of International Application No. PCT/KR2018/000545, filed Jan. 11, 2018, and claims the benefit of Korean Patent Application No. 10-2017-0011269, filed Jan. 24, 2017, contents of which are incorporated herein by reference in their entirety for all purposes as if fully set forth below.

TECHNICAL FIELD

The present invention relates to a method for purifying phenol, and specifically, to a method for purifying phenol in which hydroxyacetone, 2-methylbenzofuran and 3-methylbenzofuran in a phenol stream are removed using organic sulfonic acid and an acyl chloride.

BACKGROUND ART

Phenol is prepared by a method comprising oxidizing an alkylaryl compound to an alkylaryl hydroperoxide, concentrating the alkylaryl hydroperoxide, subjecting the concentrated alkylaryl hydroperoxide to a cleavage reaction using an acid catalyst to produce phenol and a ketone, neutralizing the acid cleavage reaction product, and subjecting the neutralized acid cleavage reaction product to fractional distillation.

Specifically, there is known a method comprising acid-decomposing cumene hydroperoxide obtained by cumene oxidation to prepare phenol. In this method, an acid decomposition product comprises phenol and acetone as main components, and further comprises various types of by-products comprising α-methylstyrene, acetophenone, 4-cumylphenol, 2-phenyl-2-propanol, 2-methylbenzofuran, 3-methylbenzofuran and unreacted cumene, and various types of carbonyl compounds comprising small amounts of hydroxyacetone (HA) and α-phenylpropionaldehyde (α-PPA).

Acetone, unreacted cumene, α-methylstyrene, hydroxyacetone and the like in the acid decomposition product are separated into a top of a column by a distillation process using a distillation column. Phenol, a portion of α-methylstyrene, a portion of hydroxyacetone, 2-methylbenzofuran, 3-methylbenzofuran and other impurities are separated into a bottom of a column.

Hydroxyacetone separated into the bottom of the column contaminates phenol which is a final product, but it is very difficult to remove the hydroxyacetone from the phenol through the distillation process. Further, hydroxyacetone may also react with phenol to form 2-methylbenzofuran. Moreover, since 2-methylbenzofuran and 3-methylbenzofuran separated together with phenol into the bottom of the column form an azeotropic mixture, it is practically impossible to separate 2-methylbenzofuran and 3-methylbenzofuran from phenol by a distillation process.

Accordingly, in order to effectively remove hydroxyacetone, 2-methylbenzofuran and 3-methylbenzofuran in the phenol stream, a method which purifies by contacting a sulfonated styrene-divinylbenzene ion-binding resin with a phenol stream has been proposed. However, although the sulfonated styrene-divinylbenzene ion-binding resin is efficient for removal of hydroxyacetone, there is a disadvantage in that post-treatment is required to remove 2-methylbenzofuran and 3-methylbenzofuran. Accordingly, there is a demand for research on a method of efficiently removing 2-methylbenzofuran and 3-methylbenzofuran as well as hydroxyacetone in the phenol stream in one reactor.

DISCLOSURE

Technical Problem

It is an object of the present invention to provide a method for purifying phenol, in which high-purity phenol can be provided by efficiently and rapidly removing hydroxyacetone, 2-methylbenzofuran and 3-methylbenzofuran contained in a phenol stream separated into an upper portion of a distillation column in a fractional distillation process.

Technical Solution

In order to achieve the above-described object, the present invention provides a method for purifying phenol, which comprises: contacting a phenol stream comprising hydroxyacetone, 2-methylbenzofuran, 3-methylbenzofuran and phenol with an acyl chloride in the presence of an organic sulfonic acid to convert one or more selected from the group consisting of hydroxyacetone, 2-methylbenzofuran and 3-methylbenzofuran into a high boiling point compound having a boiling point higher than that of the phenol; and recovering the high boiling point compound from the phenol stream.

Advantageous Effects

According to the method for purifying phenol of the present invention, one or more selected from the group consisting of hydroxyacetone, 2-methylbenzofuran and 3-methylbenzofuran in a phenol stream are converted into a high boiling point compound having a boiling point higher than that of the phenol, and thus high-purity phenol can be easily obtained through fractional distillation.

Further, according to the method for purifying phenol of the present invention, the use of an acyl chloride allows the conversion of 2-methylbenzofuran and 3-methylbenzofuran into a high boiling point compound to proceed at a high speed, and thus removal efficiency can be excellent.

Further, according to the method for purifying phenol of the present invention, hydroxyacetone, 2-methylbenzofuran and 3-methylbenzofuran in the phenol stream can be converted into a high boiling point compound having a boiling point higher than that of phenol in one reactor, and thus it is very effective in terms of production efficiency and costs.

BEST MODE OF THE INVENTION

Hereinafter, the present invention will be described in detail in order to facilitate understanding of the present invention.

It should be understood that the terms used in the specification and the appended claims should not be construed as limited to general and dictionary meanings, but interpreted based on the meanings and concepts corresponding to technical aspects of the present disclosure on the basis of the principle that the inventor is allowed to define terms appropriately for the best explanation.

In the present invention, a high boiling point compound may be a concept including all of a high boiling point compound derived from hydroxyacetone, a high boiling point compound derived from 2-methylbenzofuran, and a high boiling point compound derived from 3-methylbenzofuran. The high boiling point compound derived from hydroxyacetone, the high boiling point compound derived from 2-methylbenzofuran, and the high boiling point compound derived from 3-methylbenzofuran may be different compounds, and may be compounds having different boiling points. However, in the present invention, the high boiling point compound may be not only a compound having a boiling point higher than phenol, but also a compound having a difference in boiling point with phenol so that the compound can be separated from phenol by fractional distillation.

A method for purifying phenol according to an embodiment of the present invention comprises contacting a phenol stream comprising hydroxyacetone, 2-methylbenzofuran, 3-methylbenzofuran and phenol with an acyl chloride in the presence of an organic sulfonic acid to convert one or more selected from the group consisting of hydroxyacetone, 2-methylbenzofuran and 3-methylbenzofuran into a high boiling point compound having a boiling point higher than that of the phenol.

The phenol stream may be a phenol stream obtained by forming a reaction mixture comprising an alkylaryl hydroperoxide and an unreacted alkylaryl compound by oxidizing an alkylaryl compound, and then subjecting a cleavage product produced by the cleavage reaction of the reaction mixture to fractional distillation.

Specifically, the phenol stream may be a phenol stream obtained by oxidizing cumene to form cumene hydroperoxide, subjecting a reaction mixture comprising cumene hydroperoxide and unreacted cumene to a cleavage reaction in the presence of an acid catalyst to prepare a cleavage product mixture comprising phenol, acetone, hydroxyacetone, 2-methylbenzofuran, 3-methylbenzofuran and other impurities, and then subjecting the cleavage product mixture to fractional distillation.

Meanwhile, the oxidation of the cumene may be generally carried out by autoxidation with air-oxygen gas such as air, oxygen-enriched air or the like. Further, the oxidation reaction may be carried out with or without an additive such as an alkali. Examples of the additive include alkali metal compounds such as sodium hydroxide (NaOH) and potassium hydroxide (KOH), alkaline earth metal compounds, alkali metal carbonates such as sodium carbonate ($Na_2CO_3$) and sodium hydrogen carbonate ($NaHCO_3$), ammonia, ammonium carbonate, etc. Further, the oxidation reaction may be carried out under conditions of a temperature from about 50 to 200° C. and a pressure from atmospheric pressure to about 5 MPa.

The oxidation of the cumene may be carried out using a plurality of oxidation reactors used in a conventional phenol process, and specifically, using three oxidation reactors. A cumene hydroperoxide-containing stream may be used by oxidizing a cumene-containing stream having a cumene concentration of 80% or more, specifically 99 wt % or more, in the presence of an oxygen-containing stream. A conventional initiator may be used to promote the oxidation of the cumene. Examples of the initiator include organic hydroperoxides such as cumene hydroperoxide and t-butyl hydroperoxide, peroxy-based free radical initiators, azo-based free radical initiators, etc.

The reaction mixture including the cumene hydroperoxide and the unreacted cumene may include 60 to 95 wt % of cumene hydroperoxide based on the total weight of the reaction mixture. Examples of the acid catalyst used in the cleavage reaction include an inorganic acid, an organic acid, an acidic ion-exchange resin, a solid acid, etc. The inorganic acid includes sulfuric acid ($H_2SO_4$), sulfur dioxide ($SO_2$) and the like, and the organic acid includes toluenesulfonic acid, benzenesulfonic acid, etc. The acidic ion-exchange resin includes a sulfonated styrene-divinylbenzene resin and the like, and the solid acid includes zeolite, alumina and the like.

The cleavage product mixture may include phenol, acetone, hydroxyacetone, 2-methylbenzofuran, 3-methylbenzofuran and by-products. The by-product may be generated in the above-described oxidation and cleavage processes. For example, the cleavage product mixture may be one or more selected from the group consisting of cumene, α-methylstyrene, methanol, acetaldehyde, formaldehyde, cumylphenol, dicumylperoxide, an α-methylstyrene dimer, mesityl oxide and phenol tar.

Meanwhile, since the cleavage product mixture passes through a cleavage reaction using an acid catalyst, pH may be too low to efficiently perform the fractional distillation. Thus, the pH of the cleavage product mixture may be adjusted to be in the range of 3 to 10, specifically 4 to 7 using a base and supplied to a distillation column, such that the cleavage product mixture is suitable for carrying out the fractional distillation, that is, a purification device such as a distillation column is not damaged, that is, the purification device is prevented from being corroded. The base may be a sodium hydroxide solution, NaOH, ammonia, ammonium hydroxide, an amine or a diamine.

The cleavage product mixture may be subjected to one or more fractional distillations to be separated into an acetone fraction and a phenol fraction.

The acetone fraction may refer to a fraction comprising the acetone as a main component. The phenol fraction may refer to a fraction comprising the phenol as a main component.

Meanwhile, the temperature at the upper end of the distillation column may be lower than the temperature at the lower end of the distillation column during the fractional distillation. Specifically, the temperature at the upper end of the distillation column may be from 65 to 115° C., and specifically, 78 to 115° C. The temperature at the lower end of the distillation column may be from 170 to 225° C., and specifically, 193 to 216° C. The internal pressure of the distillation column, that is, the operating pressure, may be from 0 to 1 kgf/cm$^2$ g. When the above-described temperature and pressure conditions are satisfied, the reflux of the cleavage product mixture in the distillation column is efficiently performed, and thus separation into the acetone fraction and the phenol fraction can be easily performed.

Here, the upper end of the distillation column is not a comprehensive representation of an upper portion of the distillation column where the acetone fraction is located, and refers to an upper end of the distillation column. The lower end of the distillation column is not a comprehensive representation of a lower portion of the distillation column where the phenol fraction is located, and refers to a lower end of the distillation column.

The acetone fraction and the phenol fraction may be recovered through the upper end and the lower end of the distillation column. The recovered phenol fraction may be the phenol stream used in the method for purifying phenol of the present invention.

The organic sulfonic acid may serve as a catalyst capable of converting the hydroxyacetone in the phenol stream into a compound having a boiling point higher than that of phenol. Further, the organic sulfonic acid may serve as a catalyst in the reaction of 2-methylbenzofuran, 3-methylbenzofuran and an acyl chloride, and specifically, in an acylation reaction.

The organic sulfonic acid may be mixed with the phenol stream to facilitate the catalytic function. Stirring may be carried out after the addition of the organic sulfonic acid into the phenol stream for homogeneous mixing.

The ratio of the number of moles of the organic sulfonic acid to the total number of moles of the hydroxyacetone, the 2-methylbenzofuran and the 3-methylbenzofuran may be 1:0.05 to 1:0.2, specifically, 1:0.07 to 1:0.1, and more specifically 1:0.08 to 1:0.09. When the above-described molar ratio is satisfied, hydroxyacetone can be easily converted into a high boiling point compound having a boiling point higher than that of phenol, and can serve as a catalyst in the reaction of 2-methylbenzofuran and 3-methylbenzofuran with the acyl chloride.

Meanwhile, hydroxyacetone may react with phenol to produce 2-methylbenzofuran and 3-methylbenzofuran. Accordingly, the recovery amount of phenol may be reduced, and 2-methylbenzofuran and 3-methylbenzofuran, which have to be removed, may be increased. Hydroxyacetone may react with phenol at temperatures and acidic conditions for converting 2-methylbenzofuran and 3-methylbenzofuran into a high boiling point compound, which is removable from the phenol by fractional distillation, to produce more 2-methylbenzofuran and 3-methylbenzofuran, but the content of the resulting 2-methylbenzofuran and 3-methylbenzofuran may be reduced over time due to reaction with the acyl chloride.

As the organic sulfonic acid, a low molecular weight organic sulfonic acid is suitable, which may be used as a catalyst in the reaction of the acyl chloride with 2-methylbenzofuran and 3-methylbenzofuran, and which may serve as a catalyst while being homogeneously mixed in the phenol stream when hydroxyacetone, 2-methylbenzofuran and 3-methylbenzofuran are converted into a high boiling point compound in one reactor.

Accordingly, the organic sulfonic acid may be one or more selected from the group consisting of methane sulfonic acid, 3-hydroxypropane-1-sulfonic acid, benzene sulfonic acid, p-toluenesulfonic acid and camphor sulfonic acid, and more specifically, may be methane sulfonic acid.

Meanwhile, during performing the method for purifying phenol, a portion of hydroxyacetone may react with phenol in the presence of the organic sulfonic acid to be converted into 2-methylbenzofuran and/or 3-methylbenzofuran, thereby increasing the amount of methylbenzofuran. However, although methylbenzofuran derived from hydroxyacetone and methylbenzofuran present in the phenol stream may be converted into a high boiling point compound by reaction with phenol and removed, when the methylbenzofuran reacts with phenol, the purity of phenol may be lowered, and the reaction speed is low, causing the removal efficiency of methylbenzofuran to be poor.

Thus, by adding an acyl chloride, not only phenol but also the acyl chloride may be additionally involved in the reaction with methylbenzofuran. Further, since the acyl chloride reacts with methylbenzofuran more rapidly than phenol, the purity of phenol may be maintained by reducing the amount of phenol reacting with methylbenzofuran, and the reaction for converting methylbenzofuran into the high boiling point compound may be additionally performed through the acyl chloride, so that the removal speed of methylbenzofuran can be improved.

Accordingly, the removal speed of methylbenzofuran can be significantly improved compared with a case where an acyl chloride is not used during the purification of phenol. Thus, after the purification is complete, the amount of hydroxyacetone, 2-methylbenzofuran and 3-methylbenzofuran in the phenol stream can be significantly reduced.

As shown in the following Reaction Schemes 1 to 4, the acyl chloride may contact 2-methylbenzofuran and 3-methylbenzofuran in the presence of the organic sulfonic acid to convert 2-methylbenzofuran and 3-methylbenzofuran into a high boiling point compound having a boiling point higher than that of phenol.

<Reaction Scheme 1>

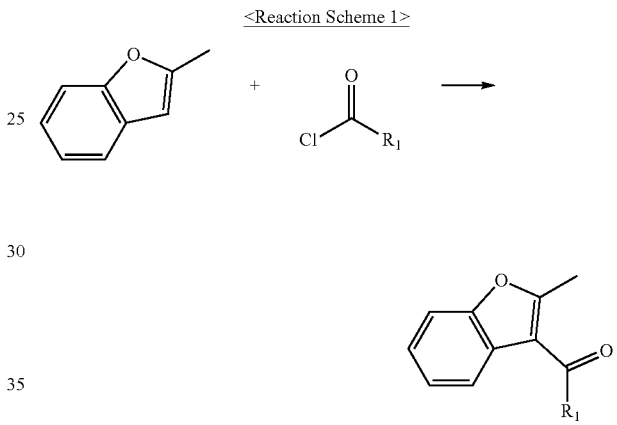

<Reaction Scheme 2>

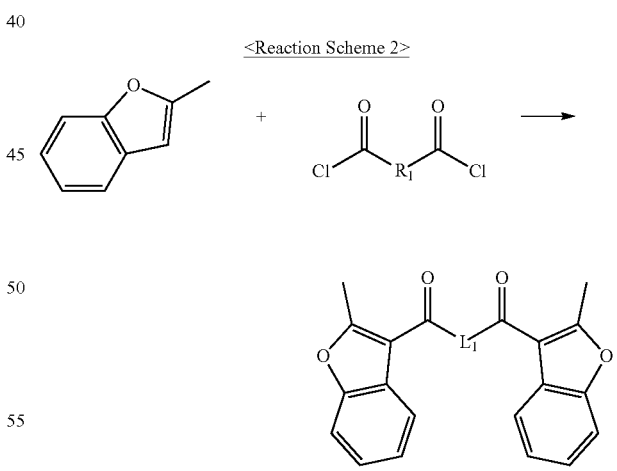

<Reaction Scheme 3>

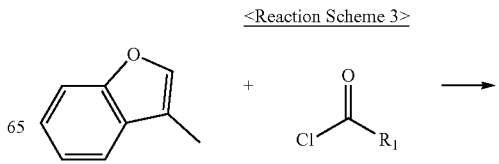

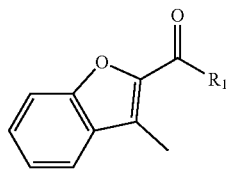

<Reaction Scheme 4>

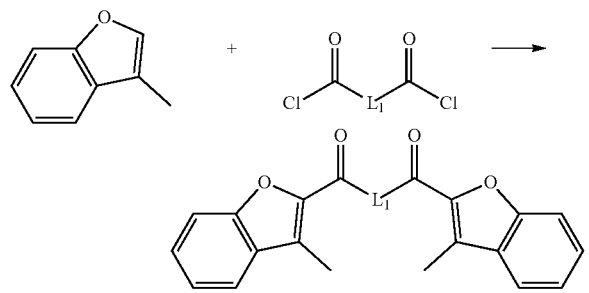

The acyl chloride may be one or more selected from the group consisting of acetyl chloride, propionyl chloride, benzoyl chloride, malonyl chloride, succinyl chloride, glutaryl chloride, adipoyl chloride, pimeloyl chloride, suberoyl chloride, azelaic acid dichloride, sebacoyl chloride, and dodecanedioyl dichloride. When an acyl chloride containing two or more

is used during the reaction of 2-methylbenzofuran and the 3-methylbenzofuran, the 2-methylbenzofuran and 3-methylbenzofuran may be converted into a high boiling point compound having a boiling point further higher than phenol.

Further, the ratio of the number of moles of the acyl chloride to the sum of the number of moles of the hydroxyacetone, 2-methylbenzofuran and 3-methylbenzofuran may be 0.5:1 to 14:1, specifically 0.7:1 to 7:1, and more specifically 1:1 to 6:1. When the above-described range is satisfied, an acylation reaction is easily initiated, the reaction rate is maintained appropriately, and the acyl chloride which does not participate in the acylation reaction can be minimized The contacting may be performed at a temperature from 50 to 90° C., specifically 60 to 80° C., and more specifically 70 to 80° C. When the above-described conditions are satisfied, the acylation reaction can be easily performed, and energy efficiency can also be improved.

The method for purifying phenol according to one embodiment of the present invention comprises recovering the high boiling point compound from the phenol stream.

The high boiling point compound may be recovered by fractional distillation. Since the high boiling point compound is recovered from the phenol stream, high-purity phenol can be obtained.

MODE OF THE INVENTION

Now, the present invention will be described in more detail with reference to the following examples. These examples are provided only for illustration of the present invention and should not be construed as limiting the scope and spirit of the present invention.

Examples 1 to 3, Comparative Examples 1 and 2: Method of Purifying Phenol 140 g of a phenol stream containing impurities such as hydroxyacetone, 2-methylbenzofuran and 3-methylbenzofuran in the amounts shown in the following Table 1 was added to a reactor and heated to 50° C. Here, methanesulfonic acid was added thereto in the amounts shown in Table 1 and stirred for 15 minutes. Then, an acyl chloride was added in the amounts shown in the following Table 1, the external temperature was set to 70° C., and the reaction was carried out for 6 hours to purify the phenol.

TABLE 1

| | Phenol stream | | | | | | |
|---|---|---|---|---|---|---|---|
| Classification | Hydroxy-acetone (ppm) | 2-methyl-benzofuran (ppm) | 3-methyl-benzofuran (ppm) | Total amount of impurities (ppm) | Methane sulfonic acid (g) | Acyl chloride Types | Content (g) |
| Example 1 | 1,175.8 | 26.9 | 5.7 | 1,208.4 | 2.44 | Adipoyl chloride | 0.45 |
| Example 2 | 1,085.4 | 24.8 | 5.4 | 1,115.6 | 2.41 | Adipoyl chloride | 2.25 |
| Example 3 | 586.4 | 18.3 | 1.9 | 606.6 | 1.17 | Adipoyl chloride | 3.36 |
| Comparative Example 1 | 984.5 | 24.5 | 4.5 | 1,013.5 | 2.13 | — | — |
| Comparative Example 2 | 586.4 | 18.3 | 1.9 | 606.6 | 1.17 | Adipoyl chloride | 0.06 |

Experimental Example 1: Analysis of Components in Phenol Stream

The amounts of hydroxyacetone, 2-methylbenzofuran and 3-methylbenzofuran in the phenol stream of the examples and comparative examples according to the reaction time were analyzed by gas chromatography. The results are shown in the following Tables 2 to 6.

TABLE 2

| | Example 1 | | | | | | | |
|---|---|---|---|---|---|---|---|---|
| | Hydroxyacetone | | 2-methylbenzofuran | | 3-methylbenzofuran | | Impurities | |
| Time | Content (ppm) | Removal rate (%) | Content (ppm) | Removal rate (%) | Content (ppm) | Removal rate (%) | Total amount (ppm) | Removal rate (%) |
| 0 | 1,175.8 | — | 26.9 | 5.7 | | — | 1,208.4 | — |
| 1 hours | 253.9 | 87.41 | 12.1 | 55.02 | 242.4 | — | 508.4 | 57.93 |
| 2 hours | 61.0 | 94.81 | 7.3 | 72.86 | 276.5 | — | 344.8 | 71.47 |
| 3 hours | 24.4 | 97.92 | 7.3 | 72.86 | 266.1 | 3.76 | 297.8 | 75.36 |
| 4 hours | 5.8 | 99.51 | 7.4 | 72.49 | 253.0 | 8.50 | 266.2 | 77.97 |
| 5 hours | 4.3 | 99.63 | 6.5 | 75.83 | 221.6 | 19.86 | 232.4 | 80.77 |
| 6 hours | 3.2 | 99.72 | 6.3 | 76.57 | 202.4 | 26.80 | 211.9 | 82.46 |
| Average removal speed | 195.4 ppm/hour | | 3.4 ppm/hour | | 18.5 ppm/hour | | 166.1 ppm/hour | |

TABLE 3

| | Example 2 | | | | | | | |
|---|---|---|---|---|---|---|---|---|
| | Hydroxyacetone | | 2-methylbenzofuran | | 3-methylbenzofuran | | Impurities | |
| Time | Content (ppm) | Removal rate (%) | Content (ppm) | Removal rate (%) | Content (ppm) | Removal rate (%) | Total amount (ppm) | Removal rate (%) |
| 0 | 1,085.4 | — | 24.8 | — | 5.4 | — | 1,115.6 | — |
| 1 hours | 70.0 | 93.55 | 6.2 | 75.00 | 245.7 | — | 321.9 | 71.15 |
| 2 hours | 7.0 | 99.35 | 5.3 | 78.62 | 245.6 | 0.04 | 257.9 | 76.88 |
| 3 hours | 2.8 | 99.74 | 4.4 | 82.25 | 216.9 | 11.72 | 224.1 | 79.91 |
| 4 hours | 1.7 | 99.84 | 4.6 | 81.45 | 187.0 | 23.89 | 193.3 | 82.67 |
| 5 hours | 1.4 | 99.87 | 5.3 | 78.62 | 173.8 | 29.26 | 180.5 | 83.82 |
| 6 hours | 1.1 | 99.89 | 4.9 | 80.24 | 163.2 | 33.58 | 114.9 | 89.70 |
| Average removal speed | 180.7 ppm/hour | | 3.3 ppm/hour | | 16.5 ppm/hour | | 166.8 ppm/hour | |

TABLE 4

| | Example 3 | | | | | | | |
|---|---|---|---|---|---|---|---|---|
| | Hydroxyacetone | | 2-methylbenzofuran | | 3-methylbenzofuran | | Impurities | |
| Time | Content (ppm) | Removal rate (%) | Content (ppm) | Removal rate (%) | Content (ppm) | Removal rate (%) | Total amount (ppm) | Removal rate (%) |
| 0 | 586.4 | — | 18.3 | — | 1.9 | — | 606.6 | — |
| 1 hours | 32.8 | 94.41 | 13.7 | 25.14 | 107.3 | — | 153.8 | 74.65 |
| 2 hours | 33.0 | 94.37 | 10.7 | 41.53 | 106.5 | 0.75 | 150.2 | 75.24 |
| 3 hours | 22.0 | 96.25 | 7.9 | 56.83 | 74.6 | 30.48 | 104.5 | 82.77 |
| 4 hours | 25.4 | 95.67 | 6.8 | 62.84 | 76.8 | 28.42 | 109.0 | 82.03 |
| 5 hours | 27.7 | 95.28 | 5.6 | 69.40 | 79.1 | 26.28 | 112.4 | 81.47 |
| 6 hours | 25.9 | 95.58 | 3.9 | 78.69 | 69.5 | 35.23 | 99.3 | 83.63 |
| Average removal speed | 93.4 ppm/hour | | 2.4 ppm/hour | | 7.6 ppm/hour | | 84.6 ppm/hour | |

TABLE 5

Comparative Example 1

| Time | Hydroxyacetone Content (ppm) | Hydroxyacetone Removal rate (%) | 2-methylbenzofuran Content (ppm) | 2-methylbenzofuran Removal rate (%) | 3-methylbenzofuran Content (ppm) | 3-methylbenzofuran Removal rate (%) | Impurities Total amount (ppm) | Impurities Removal rate (%) |
|---|---|---|---|---|---|---|---|---|
| 0 | 984.5 | — | 24.5 | — | 4.5 | — | 1,013.5 | — |
| 1 hours | 197.0 | 79.99 | 16.5 | 32.65 | 185.5 | — | 399.0 | 60.63 |
| 2 hours | 21.3 | 97.84 | 16.0 | 34.69 | 248.7 | — | 286.0 | 71.78 |
| 3 hours | 4.7 | 99.52 | 17.6 | 28.16 | 240.9 | 3.14 | 263.2 | 74.03 |
| 4 hours | 0 | 100 | 16.5 | 32.65 | 216.3 | 13.03 | 232.8 | 77.03 |
| 5 hours | 0 | 100 | 13.1 | 46.53 | 204.2 | 17.89 | 217.3 | 78.56 |
| 6 hours | 0 | 100 | 10.5 | 57.14 | 192.8 | 22.48 | 203.3 | 79.94 |
| Average removal speed | 328.2 ppm/hour | | 2.3 ppm/hour | | 14 ppm/hour | | 135.0 ppm/hour | |

TABLE 6

Comparative Example 2

| Time | Hydroxyacetone Content (ppm) | Hydroxyacetone Removal rate (%) | 2-methylbenzofuran Content (ppm) | 2-methylbenzofuran Removal rate (%) | 3-methylbenzofuran Content (ppm) | 3-methylbenzofuran Removal rate (%) | Impurities Total amount (ppm) | Impurities Removal rate (%) |
|---|---|---|---|---|---|---|---|---|
| 0 | 586.4 | — | 18.3 | — | 1.9 | — | 606.6 | — |
| 1 hours | 138.6 | 76.36 | 10.3 | 43.72 | 12.7 | — | 161.6 | 73.36 |
| 2 hours | 142.4 | 75.72 | 9.5 | 48.09 | 116.0 | — | 267.9 | 55.84 |
| 3 hours | 40.5 | 93.09 | 6.4 | 65.03 | 131.4 | — | 178.3 | 70.61 |
| 4 hours | 45.2 | 92.29 | 6.5 | 64.48 | 127.4 | — | 179.1 | 70.47 |
| 5 hours | 51.7 | 91.18 | 6.5 | 64.48 | 129.8 | — | 188.0 | 69.01 |
| 6 hours | 30.3 | 94.83 | 5.0 | 72.68 | 132.6 | — | 167.9 | 72.32 |
| Average removal speed | 92.7 ppm/hour | | 2.2 ppm/hour | | — | | 73.2 ppm/hour | |

3-MBF average removal speed: (Maximum concentration of 3-MBF−Final concentration of 3-MBF)/(Time required for completion of purification−Time required for maximum concentration)

HA average removal speed: (Concentration of HA before purification−Concentration of HA after completion of purification)/(Time required)

2-MBF average removal speed: (Concentration of 2-MBF before purification−Concentration of 2-MBF after completion of purification)/(Time required)

Referring to Tables 2 to 6, in the case of Examples 1 and 2, the amounts of hydroxyacetone and 2-methylbenzofuran were remarkably reduced over the reaction time. Further, it was confirmed that, in the case of 3-methylbenzofuran, due to 3-methylbenzofuran additionally generated by the reaction of hydroxyacetone with phenol, the amount of 3-methylbenzofuran increased significantly more than that contained before purification, but over time, the amount of methylbenzofuran was reduced.

It was confirmed that, in the case of Example 3 in which an excess amount of an acyl chloride was added, the removal rate of hydroxyacetone, 2-methylbenzofuran and 3-methylbenzofuran was lowered compared with Examples 1 and 2, but the removal rate of the total amount of hydroxyacetone, 2-methylbenzofuran and 3-methylbenzofuran was superior to that of Comparative Example 1.

It was confirmed that, in the case of Comparative Example 2 in which a small amount of an acyl chloride was added, the removal rate of the total amount of hydroxyacetone, 2-methylbenzofuran and 3-methylbenzofuran was lower than that of Comparative Example 1.

The invention claimed is:

1. A method for purifying phenol, comprising:
   contacting a phenol stream comprising hydroxyacetone, 2-methylbenzofuran, 3-methylbenzofuran and phenol with an acyl chloride in the presence of an organic sulfonic acid to convert one or more selected from the group consisting of hydroxyacetone, 2-methylbenzofuran and 3-methylbenzofuran into a high boiling point compound having a boiling point higher than that of the phenol; and
   recovering the high boiling point compound from the phenol stream.

2. The method of claim 1, wherein the organic sulfonic acid is present in a mixed state with the phenol stream.

3. The method of claim 1, wherein a ratio of a number of moles of the organic sulfonic acid to a total number of moles of the hydroxyacetone, the 2-methylbenzofuran and the 3-methylbenzofuran is 1:0.05 to 1:0.2.

4. The method of claim 1, wherein the organic sulfonic acid is one or more selected from the group consisting of methane sulfonic acid, 3-hydroxypropane-1-sulfonic acid, benzene sulfonic acid, p-toluenesulfonic acid and camphor sulfonic acid.

5. The method of claim 1, wherein the contacting is carried out at a temperature from 50 to 90° C.

6. The method of claim 1, wherein a ratio of a number of moles of the acyl chloride to a total number of moles of the hydroxyacetone, the 2-methylbenzofuran and the 3-methylbenzofuran is 0.5:1 to 14:1.

7. The method of claim 1, wherein the acyl chloride is one or more selected from the group consisting of acetyl chloride, propionyl chloride, benzoyl chloride, malonyl chloride, succinyl chloride, glutaryl chloride, adipoyl chloride, pimeloyl chloride, suberoyl chloride, azelaic acid dichloride, sebacoyl chloride, and dodecanedioyl dichloride.

8. The method of claim 1, wherein the recovering of the high boiling point compound is carried out using fractional distillation.

\* \* \* \* \*